(12) United States Patent
Pronk

(10) Patent No.: US 7,324,843 B2
(45) Date of Patent: Jan. 29, 2008

(54) MEDICAL IMAGING DEVICE FOR USE IN A SAFETY CRITICAL ENVIRONMENT

(75) Inventor: Bernardus Johannes Pronk, Eindhoven (NL)

(73) Assignee: Koninklijke Philips Electronics N. V., Eindhoven (NL)

( * ) Notice: Subject to any disclaimer, the term of this patent is extended or adjusted under 35 U.S.C. 154(b) by 1336 days.

(21) Appl. No.: 10/121,365

(22) Filed: Apr. 12, 2002

(65) Prior Publication Data

US 2002/0161293 A1 Oct. 31, 2002

(30) Foreign Application Priority Data

Apr. 13, 2001 (EP) .................................. 01201355

(51) Int. Cl.
*A61B 5/00* (2006.01)
(52) U.S. Cl. ....................................... 600/407; 600/425
(58) Field of Classification Search ................ 600/407, 600/427, 425; 378/62, 117, 207; 128/920; 700/21; 714/1, 3, 7, 10, 11, 13
See application file for complete search history.

(56) References Cited

U.S. PATENT DOCUMENTS 4,991,193 A * 2/1991 Cecil et al. ................. 378/117
5,054,044 A * 10/1991 Audon et al. ................. 378/91
5,553,618 A * 9/1996 Suzuki et al. ............... 600/411
5,851,182 A * 12/1998 Sahadevan .................. 600/407
6,282,264 B1 * 8/2001 Smith et al. ................. 378/189

FOREIGN PATENT DOCUMENTS

JP 03109648 A * 5/1991

\* cited by examiner

*Primary Examiner*—Ruth S. Smith
(74) *Attorney, Agent, or Firm*—Thomas M. Lundin

(57) ABSTRACT

The invention relates to a medical imaging device which includes a central control unit and a number of peripheral devices connected to the central control unit, one or more of the peripheral devices being provided with separate emergency control means which are arranged to allow the peripheral devices in question to function independently from the central control unit, the medical imaging device also being provided with an emergency control unit for controlling the emergency control means.

Figure 1:
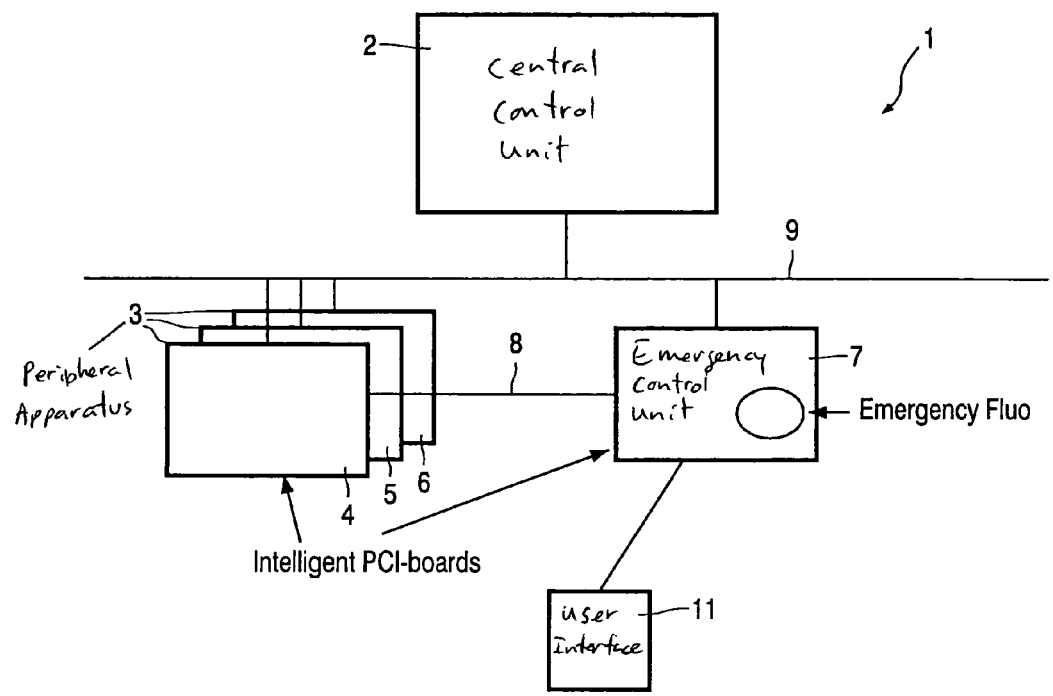

The invention also relates to a method for use of the medical imaging device according to the invention in a safety critical environment and to a computer program for carrying out the method according to the invention.

7 Claims, 1 Drawing Sheet

MEDICAL IMAGING DEVICE FOR USE IN A SAFETY CRITICAL ENVIRONMENT

BACKGROUND

The present invention relates to a medical imaging device which includes a central control unit and a number of peripheral apparatus which communicate with the central control unit.

Devices of this kind are known for a variety of applications in various technical fields. One example in this respect is a medical device for generating images of a patient, for example, in order to make a diagnosis or to provide assistance during a surgical intervention. In the interest of the patient a medical device of this kind should satisfy very severe requirements with respect to safety.

A medical imaging device of the kind set forth includes large amounts of hardware and software. For example, the central control unit is often formed by a personal computer or a workstation with software. Commercially available products are used to an increasing extent for this purpose. The amount of software necessary to control a personal computer increases every year. Because software is never completely correct or bug free, the risk of failure of the central processing unit due to a software error increases as the amount of software increases. The hardware also has a limited service life only and defects occurring therein may lead to a breakdown of the central control unit. The central control unit may become inoperative for short or long periods of time, depending on the cause. This may have detrimental effects on the safety of the patient, because the central control unit controls the peripheral apparatus which include medical imaging equipment in the present example, for example, X-ray equipment.

SUMMARY

It is an object of the present invention to provide a device of the kind set forth which is arranged to minimize the period of time during which the device is completely out of service after a breakdown of the central control unit.

To this end, one or more of the peripheral apparatus in the device in accordance with the invention are provided with separate emergency control means which are arranged to allow the peripheral apparatus provided with emergency control means to operate independently from the central control unit, the device also being provided with an emergency control unit for controlling the emergency control means. Providing a number of peripheral apparatus with emergency control means designates such apparatus as being essential. The emergency control unit takes over a part of the tasks of the central control unit, for example, the control of and the communication with and between the essential peripheral apparatus necessary for the operation of the medical imaging device. In the case of failure of the central control unit, the essential peripheral apparatus can operate without intervention by the central control unit. Moreover, such essential peripheral apparatus usually comprises less software so that they have a shorter starting-up time and hence can become operative faster than the central control unit.

The emergency control unit in a first preferred embodiment includes a processor with software which is arranged to control the peripheral apparatus provided with emergency control means in an emergency mode. Such an emergency mode may involve, for example, a minimum functionality of the relevant essential peripheral apparatus which suffices to ensure the safety of the patient.

The emergency control unit in a practical preferred embodiment is formed by the interface unit which connects the central control unit to the peripheral apparatus. Such an interface unit is present anyway and can operate separately from the central control unit.

Each of the emergency control means in a further preferred embodiment includes a separate processor with software for controlling the relevant essential peripheral apparatus in an emergency mode.

The emergency control means in an elegant preferred embodiment are plug-in cards, for example, of the PCI type. Plug-in cards of this kind are readily accessible, thus offering advantages inter alia for maintenance, repair and/or replacement, for example, for an upgrade. Said plug-in cards are commercially available and can be economically made suitable for use in conjunction with the present invention.

The emergency control unit in a further preferred embodiment is connected to the peripheral apparatus provided with emergency control means by way of separate bus connections. Because of the use of own bus connections instead of the bus connections already existing between the peripheral apparatus and the central control unit, suitable operation of the medical imaging device in an emergency situation is ensured even better.

An example of a medical imaging device includes an X-ray source, an X-ray detector and image processing means for forming an X-ray image, the X-ray source, the X-ray detector and the image processing means all being provided with separate emergency control means.

The invention also relates to a method of forming a medical image by means of a device in accordance with the invention, which method includes the following steps:
 starting the emergency control unit autonomously,
 checking and synchronizing the emergency control means of the peripheral apparatus by means of the emergency control unit, and
 executing user commands by way of the emergency control unit and the emergency control means.

The invention also relates to a computer program for carrying out the method in accordance with the invention.

DRAWINGS

Figure 2:
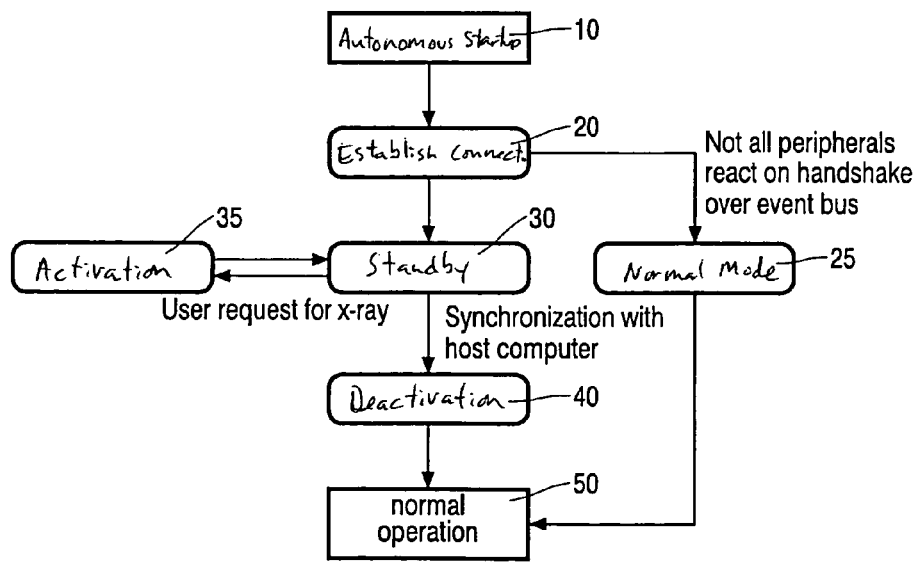

The invention will be described in detail hereinafter with reference to the drawings; therein:

FIG. 1 is a diagrammatic representation of a preferred embodiment of the device in accordance with the invention, and FIG. 2 shows a diagram illustrating the operation of the device shown in FIG. 1.

DESCRIPTION

FIG. 1 is a diagrammatic representation of a medical imaging device 1 in accordance with the invention. The device 1 includes a central processing unit 2 which communicates with a number of peripheral apparatus 3. The peripheral apparatus 3 are diagrammatically represented and, generally speaking, include all means that can be considered to be essential to the functioning of the device 1. In the preferred embodiment shown, such means are to be understood to be all means necessary to form an image of the patient. Generally speaking, such essential means include data acquisition equipment for the acquisition of patient data and image processing means for the processing and/or manipulating and display of the data. It is to be noted that, generally speaking, the composition of the essential peripheral equipment is dependent on the application. After having read the above text, any person skilled in the present technical field will be able to configure such apparatus.

The device 1 in the preferred embodiment shown is an X-ray device for the formation of images of a patient, said images being intended for medical applications. For the purpose of illustration, the data acquisition equipment of the preferred embodiment shown includes, for example, an X-ray source 4 and an X-ray detector 5. The image processing means are denoted by the reference numeral 6 and include, generally speaking, for example, an image processing unit and an image display unit.

During normal operation of the device 1 the central processor unit 2 communicates with the peripheral apparatus 3 via bus connections 9 and the interface unit 7. The object may be, for example, to provide assistance for interventional operations such as the introduction of a catheter into a patient. User commands can be entered by way of user interfaces 11 such as a keyboard or a mouse.

In the case of a breakdown of the central control unit 2, the device 1 will be out of operation for a short or longer period of time. In accordance with the invention, however, the interface unit 7 restarts very soon, that is, preferably within a few tens of seconds. The interface unit 7 then acts as an emergency control unit or an emergency interface unit. The emergency interface unit takes over a part of the tasks of the central control unit 2, for example, the control of and the communication with and between the essential peripheral apparatus 3 which are necessary for operation of the device 1. To this end, the emergency interface unit 7 includes a suitable processor with suitable programs or software. The emergency interface unit 7 communicates with the essential peripheral apparatus 3, in this case being the X-ray source 4, the X-ray detector 5 and the image processing means 6, by way of separate bus connections 8. Each of the essential peripheral apparatus 3 is provided with separate emergency control means (not shown). The emergency control means are arranged for autonomous control of the relevant peripheral apparatus and include at least a processor with suitable software which allows the associated peripheral apparatus to function independently from the central control unit. The emergency control means may also be provided with electronic circuitry which is known per se and is necessary for operation of the relevant peripheral apparatus. Alternatively, the emergency control means may form an interface to a further peripheral apparatus having a comparable function. Preferably, the emergency control means are formed by plug-in cards which are known in this technical field. The type is dependent on the hardware configuration and may be PCI, VME or any other suitable type.

In the situation shown it suffices for the essential peripheral apparatus 3 to function in an emergency mode. This means that the device 1 offers the minimum functionality required to ensure the safety of the patient. For the preferred embodiment of an X-ray device as shown this means that the X-ray source 4, the X-ray detector 5 and the image processing means 6 function in such a manner that images of adequate quality can be formed of the patient. The processor and associated software of the emergency control unit 7 and the emergency control means are adequate for this purpose.

It is to be noted that other means could also perform the function of said emergency interface unit, that is, the control of the essential peripheral apparatus. For example, the functionality of the emergency interface unit could be added to the emergency control means of one (or more) of the peripheral apparatus. The relevant peripheral apparatus should communicate with the other peripheral apparatus provided with emergency control means.

FIG. 2 shows the main steps carried out by the programs or software of the emergency interface unit 7 in response to a failure of the central control unit 2. The emergency interface unit 7 is autonomously started up in the step 10. Upon starting up, the emergency interface unit 7 establishes, in the step 20, a connection with the essential peripheral apparatus 3 and checks whether the emergency control means are available. This check can be carried out, for example, by means of a handshake protocol which is known per se. If necessary, the emergency control means are synchronized. In the step 30 the emergency interface unit 7 and the emergency control means are standby. Activation is awaited, for example, by way of a user command from step 35, for example, a request for X-rays by the user. The user can make such a request by way of the user interfaces 11 as shown in FIG. 1. In the emergency mode the request is carried out by means of the emergency interface unit 7 and the emergency control means. The central control unit 2 is provided with means for deactivating the emergency interface unit 7, the emergency control means of the essential peripheral apparatus 3 and the associated software. If a situation occurs where the central control unit 2 functions again after some time, said deactivation means are switched on in the step 40. In the step 50 device 1 then returns from the emergency mode to the normal mode of operation. It is to be noted that the device 1 in the described preferred embodiment is always standby in the emergency mode for some time upon starting up. When a user command fails to appear and the central control unit functions normally, the device 1 will subsequently change over to the normal mode of operation.

The step 25 deals with the situation in which the emergency control means and/or the emergency control unit are not ready to make the device 1 operate in the emergency mode. In that case the device 1 can function only in the normal mode of operation and awaits a change-over to the step 50.

The present invention is particularly suitable for use in conjunction with a variety of medical imaging devices which are intended for operation in an environment where safety is the most important factor. Generally speaking, at least the data acquisition equipment and the image processing means thereof should be provided with emergency control means. A so-called cardiovascular X-ray device for carrying out computed tomography forms an example of a further X-ray device in which the invention can be used. To this end, the data acquisition equipment (such as the X-ray equipment) and the image processing means should be provided with emergency control means. The invention is also suitable, for example, for use in MRI devices. The data acquisition equipment, such as a gradient amplifier, an RF amplifier, an RF receiver and the image processing means, such as a reconstructor and possibly a monitor, of such an MRI device should be provided with emergency control means in the context of the invention. In the cited examples the emergency mode enables the formation of images of the patient to be continued, be it perhaps to a limited extent.

Summarizing, it may be stated that the invention teaches an one skilled in the art to make a medical imaging device of the described kind, being intended for use in a safety critical environment, operate in an emergency mode in the case of failure of the central control unit. To this end, the essential peripheral apparatus, being controlled by the central control unit in the normal mode of operation, are provided with emergency control means for making the relevant peripheral apparatus function independently from said central control unit. A separate control unit is provided for controlling the peripheral apparatus.

After having taken notice of the foregoing, a person skilled in the art will be readily capable of carrying out the invention in practice. Hardware suitable for this purpose, such as processors, bus connections and electronic circuitry is well known in this technical field. The development of the necessary software as mentioned will not be problematic either for such a skilled person. The design of such software may be inspired by the hardware and/or software provided in the devices which are known for use in a safety critical environment in this technical field and all functionality which is superfluous for the purpose of the invention can be removed therefrom.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A medical imaging device comprising:
   a central control unit for controlling the medical imaging device;
   a plurality of peripheral apparatus for the operation of the medical imaging device, the plurality of peripheral apparatus in operative communication with the central control unit, one or more of the peripheral apparatus being provided with emergency control means which are arranged to allow the peripheral apparatus to operate independently from the central control unit; and
   an emergency control unit for controlling the emergency control means independently from the central control unit.

2. A medical imaging device as claimed in claim 1, in which the emergency control unit includes a processor for controlling the peripheral apparatus provided with emergency control means in an emergency mode.

3. A medical imaging device as claimed in claim 2, in which the emergency control unit is formed by an interface unit which provides a connection from the central control unit to the peripheral apparatus.

4. A medical imaging device as claimed in claim 3, in which the emergency control unit and the peripheral apparatus provided with emergency control means are connected by way of separate bus connections.

5. A medical imaging device as claimed in claim 2, in which each of the emergency control means includes a separate processor for controlling the relevant peripheral apparatus in an emergency mode.

6. A medical imaging device as claimed in claim 5, in which the emergency control means are plug-in cards.

7. A medical imaging device as claimed in claim 1, which device includes an X-ray source, an X-ray detector and image processing means for forming an X-ray image, the X-ray source, the X-xay detector and the image processing means each having separate emergency control means.

* * * * *